United States Patent [19]

Sartori et al.

[11] Patent Number: 5,396,019
[45] Date of Patent: Mar. 7, 1995

[54] FLUORINATED POLYOLEFIN MEMBRANES FOR AROMATICS/SATURATES SEPARATION

[75] Inventors: Guido Sartori; Win-Sow W. Ho, both of Annandale; Robert E. Noone, Neshanic Station; Bruce H. Ballinger, Bloomsbury, all of N.J.

[73] Assignee: Exxon Research Engineering Company, Florham Park, N.J.

[21] Appl. No.: 155,446

[22] Filed: Nov. 19, 1993

Related U.S. Application Data

[63] Continuation-in-part of Ser. No. 930,563, Aug. 14, 1992, abandoned.

[51] Int. Cl.$^6$ .............................................. C07C 7/144
[52] U.S. Cl. .................................... 585/819; 208/308; 585/818; 210/649; 210/650; 210/651
[58] Field of Search ............... 208/308; 585/818, 819; 210/649, 650, 651, 500.36, 500.42

[56] References Cited

U.S. PATENT DOCUMENTS

| | | | |
|---|---|---|---|
| 2,667,474 | 1/1954 | Miller | 528/481 |
| 2,965,619 | 12/1960 | Honn | 525/326.3 |
| 3,062,905 | 11/1962 | Jennings et al. | 585/819 |
| 3,966,834 | 6/1976 | Perry et al. | 208/308 |
| 4,203,848 | 5/1980 | Grandine, II | 210/500.42 |
| 4,885,096 | 12/1989 | Black | 210/640 |
| 5,022,990 | 6/1991 | Doi et al. | 210/500.42 |

FOREIGN PATENT DOCUMENTS 0394193 10/1990 European Pat. Off.
1153164 3/1958 France.

OTHER PUBLICATIONS

Journal of Membrane Science vol. 30, No. 1, Jan. 1987, Amsterdam, N. L. pp. 111–116 F. P. McCandless 'Separation of C8 Aromatic Isomers by Pervaporation through Commercial Polymer Films'.
Patent Abstracts of Japan, vol. 16, No. 352 (E-1241) 29 Jul. 1992 and JA-A-04107957 (Sumitomo Bakelite Co. Ltd.) 9 Apr. 1992.
Patent Abstracts of Japan vol. 15, No. 211 (C-836) 29 May 1991 and JP-A-03 060 725 (Toray Ind. Inc.) 15 Mar. 1991.
Patent Abstracts of Japan vol. 9, No. 21 (C-263)(1744) 29 Jan. 1985 & JP-A-59 169 512 (Nippon Oil Seal KKK) 25 Sep. 1984.
Ind. Eng. Chem. Process Des. Develop. vol. 12, No. 3, 1973 pp. 354–359 F. P. McCandless 'Separation of Aromatics & Naphthenes by Permeation through Modified Vinylidene Fluoride Films'.

Primary Examiner—Helen M. S. Sneed
Assistant Examiner—Walter D. Griffin
Attorney, Agent, or Firm—Ronald D. Hantman

[57] ABSTRACT

The present invention includes the use of crosslinked fluorinated polyolefin membranes membranes for the separation of aromatics from saturates, wherein aromatics can contain sulfur and nitrogen.

7 Claims, No Drawings

FLUORINATED POLYOLEFIN MEMBRANES FOR AROMATICS/SATURATES SEPARATION

CROSS REFERENCE TO RELATED APPLICATION

The present application is a continuation-in-part of U.S. Ser. No. 930,563, filed Aug. 14. 1992, now abandoned.

BACKGROUND

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient drive force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type, i.e., aromatic, unsaturated, and saturated, by permeating a portion of the mixture through a non-porous cellulose ether membrane and removing permeate from the permeate side of the membrane using a sweep gas or liquid. Feeds include hydrocarbon mixtures, e.g., naphtha (including virgin naphtha, naphtha from thermal or catalytic cracking, etc.).

U.S. Pat. No. 2,930,754 teaches a method for separating hydrocarbons, e.g., aromatic and/or olefinic, from gasoline-boiling range mixtures by the selective permeation of the aromatic through certain nonporous cellulose ester membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation. U.S. Pat. Nos. 5,028,685 and 5,093,003 disclose halogenated polyurethanes and membranes therefrom for separating aromatics from saturates.

U.S. Pat. Nos. 4,944,880 and 4,990,275 describe polyimide/aliphatic polyester copolymers and membranes therefrom for the separation of aromatics from saturates. U.S. Pat. Nos. 4,946,594 and 4,997,906 describe crosslinked copolymers of aliphatic polyester diols and dianhydrides and membranes therefrom for the separation of aromatics from saturates.

U.S. Pat. No. 4,976,868 discloses the use of polyester membranes (e.g., polyethylene terephthalate, polybutylene terephthalate, and polyethylene terephthalate/cyclohexane-dimethanol terephthalate) for aromatics/saturates separation. U.S. Pat. Nos. 5,012,036, 5,012,035 and 5,019,666 teach the use of polyarylate, polyphthalatecarbonate, and nonporous polycarbonate membranes, respectively, to separate aromatics from saturates, U.S. Pat. No. 5,055,631 discloses sulfonated polysulfone membranes for the separation of aromatics from saturates. U.S. Pat. No. 5,128,439 describes saturated polyesters and crosslinked membranes therefrom for aromatics/saturates separation.

U.S. Pat. No. 3,966,834 disclose the separation of dienes from organic mixtures using uncrosslinked membranes.

In 1973, F. P. McCandless (*Ind. Eng. Chem. Process Des. Develop.,* 12 (3), 354 (1973)) published a paper on the separation of aromatics from naphthenes by permeation through modified polyvinylidenefluoride membranes. The modifying agent was 3-methyl-sulfolane used as a plasticizer. The maximum temperature used by McCandless was 100° C. In practice, the membranes described by McCandless cannot have suitable stability; the plasticizer would be slowly leached out and contaminate the permeate, and the membrane performance would change with time.

In a subsequent paper, McCandless et al (*Ind. Eng. Chem. Process Des. Develop.,* 13 (3), 310 (1974)) investigated the separation of benzene from cyclohexane using a solvent-modified polyvinylidenefluoride film via adding the solvent in the hydrocarbon feed. The solvents were dimethylformamide (DMF) or dimethylsulfoxide. Such a solvent-modified membrane process cannot be practical in industrial use as it would require the separation of the solvent from the permeate and retentate.

The present invention describes the use of crosslinked fluorinated polyolefin membranes for the separation of aromatics from saturates. As will result from the examples, the crosslinked membranes covered by this invention can be used at temperatures well above those used by McCandless. The word "aromatics" includes, in addition to aromatic hydrocarbons, also heteroatom cyclic compounds containing sulfur and nitrogen.

Compared to distillation, membrane permeation can lead to considerable energy savings. A membrane can separate a mixture of aromatics and saturates, e.g., a heavy catalytic naphtha, into a high-octane, mainly aromatic permeate and a high-cetane, mainly saturated retentate. Both permeate and retentate are more valuable than the starting heavy catalytic naphtha.

SUMMARY OF THE INVENTION

The present invention includes a method to crosslink fluorinated polyolefin membranes by thermal treatment and the use of crosslinked fluorinated polyolefin membranes for the separation of aromatics from saturates. The aromatics can contain sulfur and nitrogen.

The membrane may be crosslinked by heating above about 100° C. prior to contacting with the aromatic/saturate mixture or during the contacting step with in situ crosslinking. The in situ crosslinked membrane continues to contact the mixture for further separation.

DESCRIPTION OF THE PREFERRED EMBODIMENT

The fluorinated polyolefins useful according to the present invention preferably melt below 250° C., more preferably below 200° C. Examples of homopolymers are polyvinylidenefluoride, polyvinylfluoride, and polytrifluoroethylene. The present invention also covers the use of copolymers of fluorolefins with each other, e.g., vinylidenefluoride with hexafluoropropylene or copolymers with olefins, e.g., a nearly alternating copolymer of chlorotrifluoroethylene with ethylene available commercially under the name of Halar.

Membranes can be prepared by extrusion or by solution casting.

Fluorinated polyolefins require crosslinking before use or undergo crosslinking during use, as described in the examples.

The membranes are useful for the separation of aromatics, including sulfur and nitrogen heteroatom cyclic compounds, from saturates in petroleum and chemical streams, and have been found to be particularly useful for the separation of large substituted aromatics from saturates as are encountered in heavy catalytic naphtha streams boiling at 140° C.–235° C. Other streams which are also suitable feed streams for aromatics/saturates separation are intermediate catalytic naphtha streams boiling at 93° C.–160° C., light aromatics content streams boiling in the 40° C.–150° C. range, light catalytic cycle oil boiling in the 200° C.–345° C. range, jet fuel boiling in the 140° C.–280° C. range, diesel boiling in the 200° C.–365° C. range as well as streams in chemical plants which contain recoverable quantities of benzene, toluene, xylenes (BTX) or other aromatics in combination with saturates. Combinations of above streams are also suitable feed streams. Examples of sulfur-containing aromatics are thiophene, benzothiophene, dibenzothiophene and their alkyl derivatives. Examples of nitrogen-containing aromatics are aniline, pyridine, quinolines, acridine, 7,8-benzoquinoline and their alkyl derivatives. The separation techniques which may successfully employ the membranes of the present invention include perstraction and pervaporation.

Perstraction involves the selective dissolution of particular components contained in a mixture into the membrane, the diffusion of those components through the membrane, and the removal of the diffused components from the downstream side of the membrane by the use of a liquid sweep stream. In the perstractive separation of aromatics from saturates in petroleum or chemical streams, the aromatic molecules present in the feed stream dissolve into the membrane film more easily than the saturates, due to similarities between the membrane solubility parameter and those of the aromatic species in the feed. The aromatics then permeate (diffuse) through the membrane and are swept away by a sweep liquid which is low in aromatics content. This keeps the concentration of aromatics at the permeate side of the membrane film low and maintains the concentration gradient which is responsible for the permeation of the aromatics through the membrane.

The sweep liquid is low in aromatics content so as not to itself decrease the concentration gradient. The sweep liquid is preferably a saturated hydrocarbon liquid with a boiling point much lower or much higher than that of the permeate aromatics. This is to facilitate separation, as by simple distillation. Suitable sweep liquids, therefore, would include, for example $C_3$ to $C_6$ saturated hydrocarbons and lube base stocks ($C_{15}$–$C_{20}$).

The perstraction process is run at any convenient temperature, preferably as low as possible.

The choice of pressure is not critical since the perstraction process is not dependent on pressure, but on the ability of the aromatic components in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not. If $C_3$ or $C_4$ sweep liquids are used at 25° C. or above in liquid state, the pressure must be increased to keep them in the liquid phase.

Pervaporation, by comparison, is run at generally higher temperatures than perstraction and relies on vacuum on the permeate side to evaporate the permeate from the surface of the membrane and maintain the concentration gradient driving force which drives the separation process. As in perstraction, the aromatic molecules present in the feed dissolve into the membrane film, migrate through said film and emerge on the permeate side under the influence of a concentration gradient. Pervaporation separation of aromatics from saturates can be performed at a temperature of about 25° C. for the separation of benzene from hexane but for separation of heavier aromatics/saturate mixtures, such as heavy catalytic naphtha, higher temperatures of at least 80° C. and higher, preferably at least 100° C. and higher, more preferably at least 120° C. have been successfully used with membranes prepared from fluorinated polyolefins, the maximum upper limit being that temperature at which the membrane is physically damaged. Vacuum on the order of 1–80 mm Hg is pulled on the permeate side. The vacuum stream containing the permeate is cooled to condense out the highly aromatic permeate. Condensation temperature should be below the dew point of the permeate at a given vacuum level. Instead of vacuum, a sweep gas may also be used in the permeate side.

The membrane itself may be in any convenient form utilizing any convenient module design. Thus, sheets of membrane material may be used in spiral-wound or plate-and-frame permeation cells modules. Tubes and hollow fibers of membranes may be used in bundled configuration with either the feed or the sweep liquid (or vacuum) in the internal space of the tube or fiber, the other material obviously being on the other side.

When the membrane is used in a hollow fiber configuration with the feed introduced on the exterior side of the fiber, the sweep liquid flows on the inside of the hollow fiber to sweep away the permeated highly aromatic species, thereby maintaining the desired concentration gradient. The sweep liquid, along with the aromatics contained therein, is passed to separation means, typically distillation means, however, if a sweep liquid of low enough molecular weight is used, such as liquefied propane or butane, the sweep liquid can be permitted to simply evaporate, the liquid aromatics being recovered and the gaseous propane or butane (for example) being recovered and reliquefied by application of pressure or lowering of temperature.

The membranes are used to separate aromatics from saturates in a pervaporation apparatus. The pervaporation apparatus is a cell, separated into two compartments by a porous metal plate, on which the membrane is supported. During a pervaporation experiment the aromatics/saturates mixture is circulated through the upper compartment at the desired temperature. The lower compartment is kept at atmospheric pressure and swept with a slow stream of inert gas, e.g., argon, which carries the permeate to a gas chromatograph for analysis. Otherwise, the lower compartment is kept under vacuum and the permeate goes directly to a mass spectrometer for analysis or is condensed in a trap and then analyzed by gas chromatography. In our experiments the feed is a toluene/n-octane mixture containing the two hydrocarbons in approximately equal weights.

The following examples illustrate the invention without limiting it.

EXAMPLE 1

20 g of polyvinylidenefluoride known under the commercial name of Kynar 461 was dissolved in 85 g of dimethylformamide (DMF). The thick solution so obtained was cast on a Gore-Tex ® (porous Teflon) support. After most of the DMF had evaporated, a membrane was heated at 100° C. and 150° C., each time for 15 hours, which led to insolubility in DMF, i.e., crosslinking.

A piece of membrane was tested in the pervaporation apparatus described above with the permeate side kept under vacuum, using a feed consisting of equal weights of toluene and n-octane. Analyses of the permeates were carried out by mass spectroscopy. The following table gives the results:

| T (°C.) | Toluene/n-Octane Separation Factor | Normalized Flux (Permeability) (Kg · μM/M² · D) |
|---|---|---|
| 150 | 6.3 | 523 |
| 170 | 6.1 | 4028 |
| 190 | 5.1 | 6480 |
| 210 | 4.5 | 9720 |

In this table, the separation factor is defined as the ratio of toluene and n-octane concentrations in the permeate divided by the ratio of toluene and n-octane concentrations in the feed. The normalized flux, i.e., permeability, is expressed in the unit of kilogram of the permeate per meter square membrane area per day for a normalized membrane thickness of 1 micron (Kg.μM/M².D).

EXAMPLE 2

A polyvinyl idenefluoride membrane was prepared and crosslinked as described in Example 1. In the permeator, the permeate side was kept at atmospheric pressure and swept with a slow stream of argon, which carried the permeate to a gas chromatograph. The following table gives the results:

| T (°C.) | Toluene/n-Octane Separation Factor | Normalized Flux (Permeability) (Kg · μM/M² · D) |
|---|---|---|
| 150 | 6.7 | 1,200 |
| 170 | 6 | 6,500 |
| 190 | 5.1 | 9,600 |
| 210 | 4.8 | 13,000 |
| 225 | 4 | 18,000 |

EXAMPLE 3

A copolymer of 65 wt % vinylidenefluoride and 35 wt % hexafluoropropylene, commercially known as Tecnoflon, was dissolved in dimethylformamide and a membrane was cast on a Gore-Tex ® support. The membrane was crosslinked by heating it as indicated below:

| T (°C.) | Hours |
|---|---|
| 100 | 16 |
| 150 | 17 |
| 200 | 16.5 |
| 250 | 33 |
| 300 | 30 |
| 320 | 30 |

The membrane so treated became insoluble in dimethylformamide, i.e., crosslinked. It was tested in the apparatus described in Example 2. The following table gives the results:

| T (°C.) | Toluene/n-Octane Separation Factor | Normalized Flux (Permeability) (Kg · μM/M² · D) |
|---|---|---|
| 150 | 3.2 | 1,500 |
| 167 | 2.3 | 1,500 |
| 187 | 2.1 | 2,300 |
| 195 | 2.0 | 2,600 |
| 215 | 1.9 | 5,600 |

EXAMPLE 4

A 2 mil thick film of polyvinylfluoride was heated at 100° C. and 150° C., each time for 15 hours, then tested in the apparatus described in Example 2. The following table gives the results:

| T (°C.) | Toluene/n-Octane Separation Factor | Normalized Flux (Permeability) (Kg · μM/M² · D) |
|---|---|---|
| 150 | 8.6 | 620 |
| 165 | 7.3 | 2,020 |
| 180 | 6.2 | 5,300 |
| 210 | 5.4 | 9,760 |
| 223 | 4.6 | 12,408 |
| 262 | 3.8 | 19,300 |

EXAMPLE 5

Polyvinylfluoride, as supplied, is soluble in dimethylformamide (DMF) at 110° C.

However, polyvinylfluoride heated at 100° C. for 15 hours and at 150° C. for another 15 hours is insoluble in DMF at 110° C.

Furthermore, a polyvinylfluoride membrane becomes insoluble in DMF at 110° C. after use showing that it became crosslinked in situ.

EXAMPLE 6

A 2 mil thick polyvinyl idenefluoride film prepared by extrusion was tested in the permeator described in Example 2. The temperature was maintained at 150° C. for 39 hours to give the membrane enough time to crosslink in situ. The following table gives the results:

| T (°C.) | Toluene/n-Octane Separation Factor | Normalized Flux (Permeability) (Kg · μM/M² · D) |
|---|---|---|
| 150 | 7.2 | 600 |
| 160 | 6.3 | 1,500 |
| 170 | 5.7 | 2,400 |
| 180 | 5.3 | 3,300 |
| 190 | 5.0 | 4,000 |
| 200 | 4.5 | 4,300 |
| 210 | 4.3 | 20,000 |

The used membrane was insoluble in dimethylformamide, i.e., it had undergone crosslinking in situ.

EXAMPLE 7

The membrane was a 2.1 mil thick film of polyvinylfluoride, previously heated at 100° C. and 150° C. for 15 hours at each temperature. The above thermal treatment crosslinked the film.

The feed contained 0.05 wt % of thiophene, 46.7% toluene, 52.7% n-octane and 0.10% quinoline.

The following table shows the results.

| Temper- | Selectivity Over n-Octane | | | Flux |
|---|---|---|---|---|
| ature °C. | Thiophene | Toluene | Quinoline | (Kg · μ/M² · D) |
| 133 | 23.5 | 8.4 | — | 118 |
| 170 | 17.2 | 7.0 | 2.5 | 1664 |
| 190 | 10.1 | 5.0 | 3.3 | 4750 |
| 217 | 7.9 | 4.3 | 3.1 | 6300 |

EXAMPLE 8

The apparatus was the same as that described in Example 1. The polyvinylfluoride membrane was 2.2 mils thick.

The feed contained 0.1 wt % thiophene, 49.9 wt % toluene, 49.9 wt % n-octane, and 0.1 wt % aniline.

The following table shows the results.

| Temperature | Selectivity Over n-Octane | | | Flux |
|---|---|---|---|---|
| °C. | Toluene | Thiophene | Aniline | (Kg · μ/M² · D) |
| 125 | 7.9 | 17.9 | 41.5 | 146 |
| 150 | 6.8 | 13.6 | 28.1 | 561 |
| 170 | 5.0 | 9.3 | 12.1 | 1638 |
| 190 | 4.2 | 7.2 | 10.5 | 4537 |
| 210 | 3.5 | 5.7 | 9.1 | 6490 |

What is claimed is:

1. A process for the separation of mixtures of aromatics and saturates into aromatics-enriched and saturates-enriched streams comprising:

a) contacting said aromatics/saturates mixture with one side of a crosslinked fluorinated polyolefin membrane at a temperature greater than 100° C.; and b) selectively permeating the aromatic components of the mixture through the membrane.

2. A process according to claim 1 wherein said fluorinated polyolefin membrane is crosslinked by heating above about 100° C. prior to said contacting step or during said contacting step with in situ crosslinking.

3. A process according to claim 1 where said fluorinated polyolefin is a homopolymer, a copolymer of two fluorinated olefins with each other or a copolymer of a fluorinated olefin with an olefin.

4. A process according to claim 3 wherein said homopolymer is polyvinylidenefluoride, polyvinylfluoride, or polytrifluoroethylene.

5. A process according to claim 3 wherein said copolymer is a vinylidenefluoride-hexafluoropropylene copolymer or is an alternating copolymer of ethylene and chlorotrifluoroethylene.

6. A process according to claim 1 wherein said aromatics/saturates mixture is selected from the group consisting of heavy catalytic naphtha boiling in the 140°-235° C. range, intermediate catalytic naphtha, boiling in the 93°-160° C. range, light aromatics streams boiling in the 40°-150° C. range, light catalytic cycle oils boiling in the 200°-345° C. range, jet fuel boiling in the 140°-280° C. range, diesel boiling in the 200°-365° C. range, streams containing benzene, toluene, xylenes, other aromatics, sulfur and nitrogen-containing heteroatom cyclic compounds, saturates, and combinations thereof.

7. The process of claim 1 wherein said feedstream includes sulfur and/or nitrogen.

* * * * *